United States Patent [19]
Fabinski et al.

[11] Patent Number: 5,486,699
[45] Date of Patent: Jan. 23, 1996

[54] NON-DISPERSIVE INFRARED SPECTROMETER

[75] Inventors: Walter Fabinski, Kriftel; Gerhard Wiegleb, Neu-Anspach; Peter Hering; Werner Fuss, both of Garching; Michael Haisch, Düsseldorf, all of Germany

[73] Assignee: Mannesmann Aktiengesellschaft, Dusseldorf, Germany

[21] Appl. No.: 372,868

[22] Filed: Jan. 13, 1995

Related U.S. Application Data

[63] Continuation of Ser. No. 96,017, Jul. 22, 1993.

[30] Foreign Application Priority Data

Jul. 22, 1992 [DE] Germany .................. 42 24 146.4

[51] Int. Cl.$^6$ .................................................. G01N 21/35
[52] U.S. Cl. ........................................ 250/345; 356/437
[58] Field of Search ............................. 250/345; 356/437

[56] References Cited

U.S. PATENT DOCUMENTS 4,298,347 11/1981 Walsh ............................................. 23/230
4,684,805 8/1987 Shu-Ti et al. ................................ 250/343

FOREIGN PATENT DOCUMENTS 60-190838 9/1985 Japan .................................... 356/437

Primary Examiner—Constantine Hannaher
Attorney, Agent, or Firm—Cohen, Pontani, Lieberman, Pavane

[57] ABSTRACT

A method and an apparatus for the selective determination of an isotope portion of a measuring gas by means of non-dispersive spectroscopy. The method includes sensitizing in a first ray path to the isotope component and sensitizing in a second ray path to the isotope-pure measuring gas, and electronically amplifying the measurement results. In order to improve the selectively and the sensitivity while maintaining a simple construction, an additional optical filtering is carried out in the first ray path by a filter filled essentially with isotope-pure measuring gas and the electronic measuring value of the second ray path is entered by influencing the amplification factor and an offset in the electronic amplification of the first ray path.

17 Claims, 3 Drawing Sheets

NON-DISPERSIVE INFRARED SPECTROMETER

This is a continuation of application Ser. No. 08/096,017, filed Jul. 22, 1993.

BACKGROUND OF THE INVENTION

1. Field of the Invention

The present invention relates to a method and an apparatus for the selective determination of an isotope portion of a measuring gas by means of non-dispersive infrared spectroscopy. The method includes sensitizing in a first ray path to the isotope component and sensitizing in a second ray path to the isotope-pure measuring gas, and electronically amplifying the measurement results.

2. Description of the Related Art

The selective determination of isotope portions has gained particular importance in the fields of biology, geology and archeology, and in recent times even in the field of medicine. The so-called $^{13}C$-Method, which has been established for a long time in the fields of geology and archeology, is utilized as a method for the determination of the age of dead matter. In addition, stable isotopes have been used for considerable time as marking in order to be able to examine metabolic processes in living matter, for example, in the field of medicine.

When using isotopes in the fields of medicine or biology, i.e., in living matter in general, it is important that stable isotopes are used. In many cases, they are the nitrogen isotope $^{15}N$ or the carbon isotope $^{13}C$. Instabile isotopes, i.e., radioactive isotopes, locally introduce energy because of the radioactive decay. This energy changes the metabolic processes or breaks up chemical bonds. In the field of medicine, the use of radioactive isotopes is generally prohibited. The use of $^{13}C$ has become popular as a marking element for the diagnostic evaluation of metabolic diseases or diseases of the gastrointestinal system in humans. Particularly successful is the use of $^{13}C$ as a marking element for the diagnostic evaluation of infectious stomach diseases, such as, helicopacter pylory infections. These infections can be diagnosed simply after a dose of $^{13}C$-marked urea through the expiration air of patients. This makes a complicated gastroscopy superfluous.

In the above-described applications as well as in other applications, mass spectrometric methods are used because of the requirements made of the selectivity of the measuring method. Because of the necessity to produce a high vacuum and because of the complicated sample preparation as well as the technically complicated design of the analyzer, these methods are expensive and, thus, are difficult to realize in many laboratories.

It is also known in the art to use a purely optical method, i.e., the non-dispersive infrared spectroscopy for the selective isotope portion determination, particularly in the determination of the $^{13}C/^{12}C$ ratio. Such a possibility has already been described in *Chemical Abstracts,* Vol. 90, 1979, No. 90:37 27 6d, Helge et al. The use and the conditioning of non-dispersive infrared spectroscopy is also known from U.S. Pat. No. 4,289,347. These known apparatus and methods have the disadvantage that the selectivity or the sensitivity of the infrared spectrometer does not always make possible a secure measurement or a secure diagnosis.

SUMMARY OF THE INVENTION

Therefore, it is the primary object of the present invention to provide a method and an apparatus for selectively determining an isotope portion of a measuring gas which significantly increase the selectivity and the measuring sensitivity, while the apparatus remains of simple construction.

In accordance with the present invention, an additional optical filtering is carried out in the first ray path by a filter filled essentially with isotope-pure measuring gas and the electronic measuring value of the second ray path is entered by influencing the amplification factor and an offset in the electronic amplification of the first ray path.

The apparatus according to the present invention includes a non-dispersive infrared spectrometer with a first and a second ray path each composed of an infrared radiator, a measuring vessel and a detector, with amplification detectors which produce at the output an electric output signal. For the selective determination of the isotope portion of a measuring gas, a filter vessel filled with gas primarily corresponding to the isotope-pure measuring gas is arranged between the measuring vessel and the detector of the first ray path. The subsequent detector is sensitized to the isotope which is proportionately to be determined. The detector of the second ray path is sensitized to the isotope-pure measuring gas.

Accordingly, the present invention utilizes the known configuration of a non-dispersive infrared spectrometer and supplements it with appropriate elements. One of the fundamental problems which must be overcome when increasing the sensitivity of a non-dispersive infrared spectrometer for the determination of isotope concentrations is the high transverse sensitivity of the marked gas and of the unmarked gas. This is caused by the great overlap of the infrared spectra which overlap, in turn, results from the low mass difference between the gases.

An additional effect which poses a problem in this connection is the carrier gas dependency. These effects are significantly reduced by the combination according to the present invention of an optical filtering with a subsequent electronic influencing of the signal.

The apparatus according to the present invention and the operation thereof will be explained in the following with the aid of the example of the $^{13}CO_2/^{12}CO_2$ measurement. However, the description is also applicable to other gases.

The optical filter is composed of an additionally arranged filter which is filled with $^{12}CO_2$ and is arranged in the first ray path in which the $^{13}CO_2$ detector is arranged. The transverse sensitivity relative to the $^{12}CO_2$ present in the measuring gas in an amount of approximately 3–5% by volume results in an indication error of up to 300 ppm. $^{13}CO_2$. It is exactly this error effect which can be minimized by utilizing the filter or the filter vessel which is filled with 100% by volume $^{12}CO_2$ and is integrated in the ray path. In this measurement arrangement, this filtration reduces the error influence from 5% by volume $^{12}CO_2$ to approximately 50 ppm. $^{13}CO_2$. The $^{12}CO_2$ concentration is measured in the second ray path. The measurement range is approximately 100 times greater than the $^{13}CO_2$ measuring range, so that transverse sensitivities of $^{13}CO_2$ are negligible in the second ray path. For correcting the remaining transverse sensitivity of the $^{13}CO_2$ duct, the electric output signal of this duct is computed with that of the $^{13}CO_2$ duct, in the manner described in the above summary of the method of the present invention. This means that there remains the influence of $_{12}CO_2$ on the $^{13}CO_2$ duct of below 1 ppm. $^{13}CO_2$ over the concentration range between 0% and 5% by volume. In addition to the described transverse sensitivity of $^{12}CO_2$, there is a carrier gas dependency which acts as an influence on the sensitivity of the $^{13}CO_2$ duct with approximately up to −5% from the measuring value/percent by volume $^{12}CO_2$.

This error influence is reduced by the positive filtering measures of the present invention to approximately −2% of the measuring value/percent by volume $^{12}CO_2$. The additional measure of the multiplicative computation of the sensitivity of the $^{13}CO_2$ duct with the $^{12}CO_2$ concentration reduces this influence to less than 1% over the concentration range of 0% to 5% by volume $^{12}CO_2$.

Because of aging phenomena in the measuring system and in new installations after transportation, there is the question of calibration by means of appropriate test gases. This calibration is carried out in accordance with the present invention by means of calibration vessels filled with the components $^{13}CO_2$ and $^{12}CO_2$. Room air which is freed of $CO_2$ is additionally added.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described a preferred embodiment of the invention.

DESCRIPTION OF THE PREFERRED EMBODIMENTS

Figure 1:
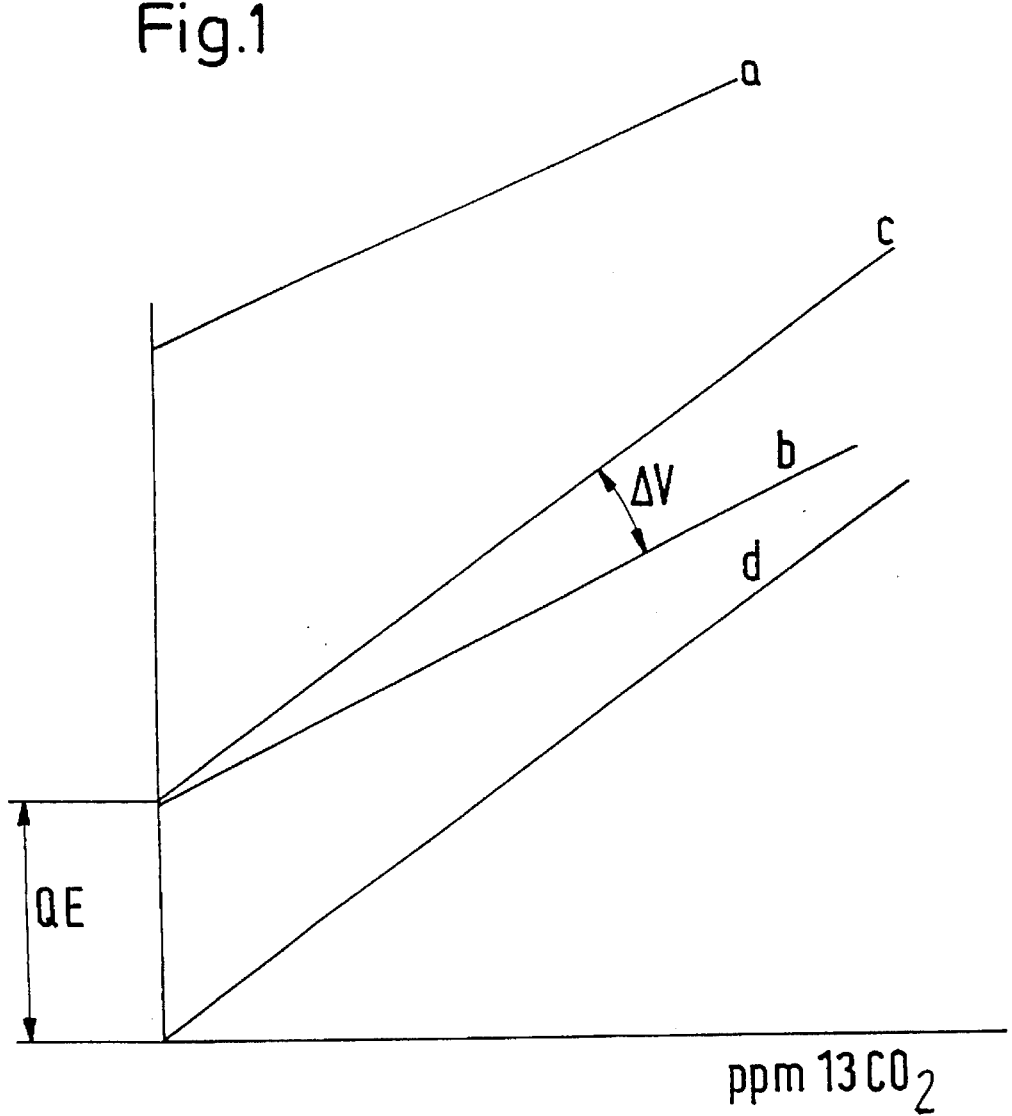
FIG. 1 is a diagram showing the output signal in dependence on the concentration of $^{13}CO_2$.

FIG. 1 of the drawings shows the output signal in arbitrary units as a function of the concentration of $^{13}CO_2$. The upper curve represents the output signal pattern a without the inventive measures, i.e., with a conventional NDIR spectrometer without additional filter vessels and without electronic compensation. The pattern b results from a pure offset shift which is caused by the additional filter vessel which is filled with $^{12}CO_2$ and is placed in the measuring ray path of the $^{13}CO_2$ duct. The subsequent electronic compensation, which shall be described in more detail below, initially causes a rotation of the curve b by an amplification factor change $\Delta V$. Consequently, the pattern b is transferred to the pattern c.

In addition, the electrical compensation causes a second parallel shift which compensates the transverse sensitivity QE and, thus, transfers the curve pattern c to the curve pattern d. Accordingly, this curve pattern d is the compensated and corrected output signal pattern. The effected rotation for transferring the pattern b to pattern c is the above-mentioned compensation of the carrier gas dependency, and the second parallel shift for transferring the pattern c to pattern d is the compensation of the transverse sensitivity. The pattern d of the output signal achieved by the compensation result corresponds to the following function:

$$yd = u * {}^{13}CO_2 \text{ (wherein } {}^{13}CO_2 \text{ is in units of a concentration)}$$

However, because of the carrier gas dependency and the transverse sensitivity, the output signal pattern is still pattern b even after the optical compensation by the filter vessel. This can be represented by the following function:

$$yd = (u * {}^{13}CO_2) * (v * {}^{12}CO_2) + w * {}^{12}CO_2.$$

In the above function, the factor $v * {}^{12}CO_2$ constitutes the carrier gas dependency which falsifies the amplification factor and represents the rotation. The term $w * {}^{12}CO_2$ constitutes the transverse sensitivity, i.e., the parallel shift QE to pattern d. For transferring the pattern b to the signal pattern d, the correction factors are introduced as follows:

$$yd' = (u * {}^{13}CO_2) * \frac{(v * {}^{12}CO_2)}{(\alpha * {}^{12}CO_2)} + (w * {}^{12}CO_2) - \beta * {}^{12}CO_2,$$

wherein $\alpha$ and $\beta$ are the correction factors and a complete correction of the carrier gas dependency takes place for $\alpha = v$, i.e., the fraction of the function yd becomes 1, and a correction of the parallel displacement takes place at $\beta = w$. This means that the function yd' corresponds to the function yd, i.e., the compensation is concluded.

Figure 2:
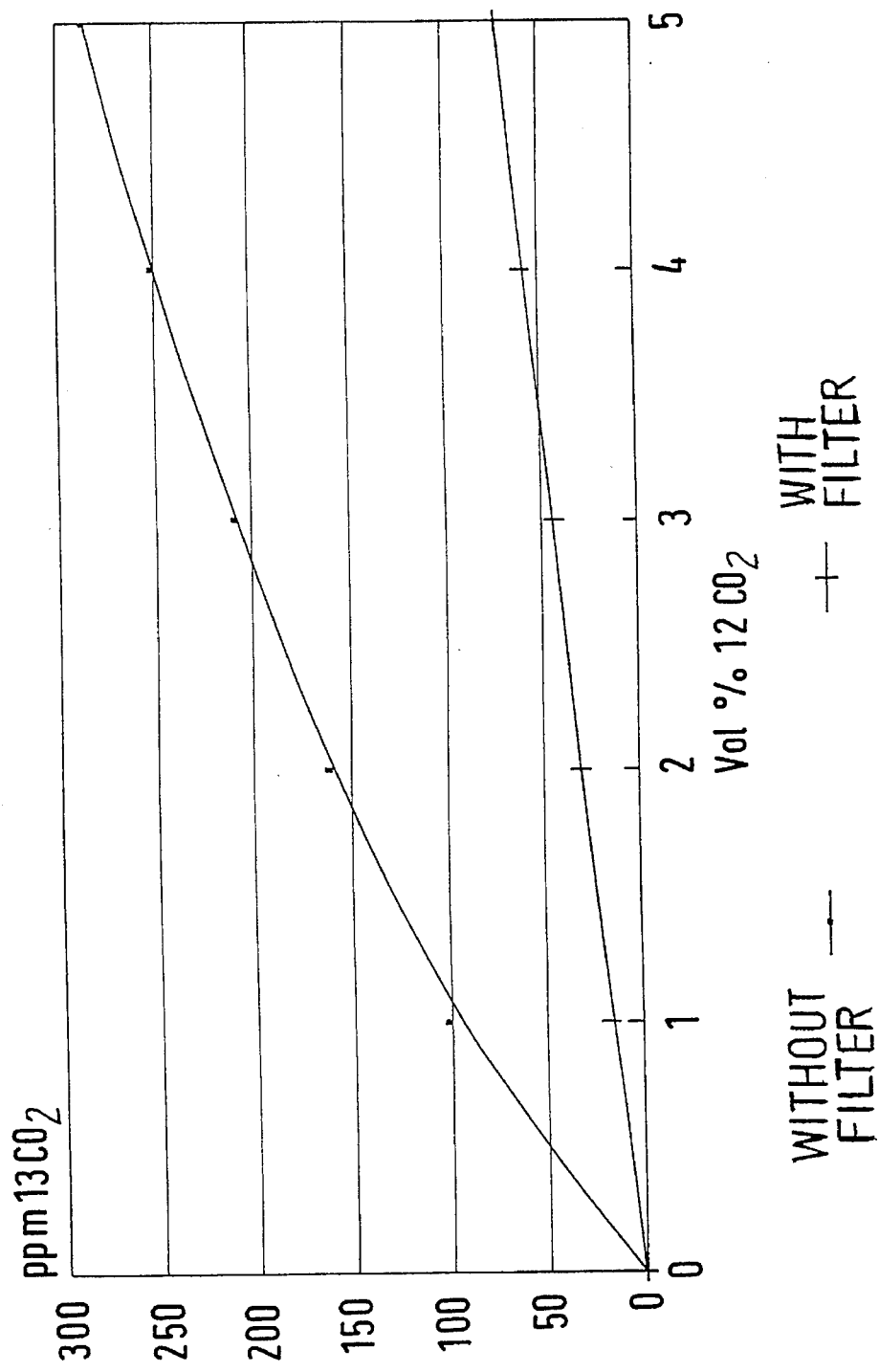
FIG. 2 is a diagram showing the transverse sensitivity of $^{12}CO_2$ against $^{13}CO_2$ with and without filter.

FIG. 2 of the drawing shows the effect of the transverse sensitivity reduction as a result of the optical and electronic measures according to present invention. Specifically, FIG. 2 shows the transverse sensitivity of $^{12}CO_2$ relative to $^{13}CO_2$. For example, the illustration of FIG. 2 shows that, in the case of a portion of 5% by volume $^{12}CO_2$, the transverse sensitivity is 300 ppm. $^{13}CO_2$. In the case of a portion of 4% by volume $^{12}CO_2$, this value corresponds to 250 ppm. $^{13}CO_2$ and, for other portions of $^{12}CO_2$, extends in accordance with the upper curve pattern. The situation illustrated in the upper curve pattern is the transverse sensitivity occurring in selective measurements of $^{13}CO_2$ to $^{12}CO_2$ by a non-dispersive infrared spectrometer. The introduction according to the present invention of the additional filter vessel FK which is filled with $^{12}CO_2$ reduces the transverse sensitivity according to the upper curve pattern in FIG. 2 to the lower curve pattern in FIG. 2. This means this reduction is initially effected without electronic compensation. It is important in this connection that the optical compensation not only reduces the magnitude of the transverse sensitivity, but, in addition to the reduction of the inclination of the transverse sensitivity curve, the curvature is also compensated out of the curve. In other words, the transverse sensitivity reduction achieved with the optical compensation means according to the present invention, the transverse sensitivity is also linearized. This linearized transverse sensitivity pattern makes it possible to carry out a linear electronic compensation of the remaining transverse sensitivity. It becomes apparent at this point that the measure of the optical compensation supplements the measure of the electronic compensation. With the subsequent electronic compensation it is achieved that the lower linear curve pattern of the transverse sensitivity essentially after-compensates to zero. The transition from the upper curve pattern to the lower curve pattern in FIG. 2 corresponds to the transition from the initial signal pattern a in FIG. 1 to the output signal pattern b in FIG. 1. The transition from the output signal pattern b to d through c takes place in the electronic manner described above in the summary of the invention.

Figure 3:
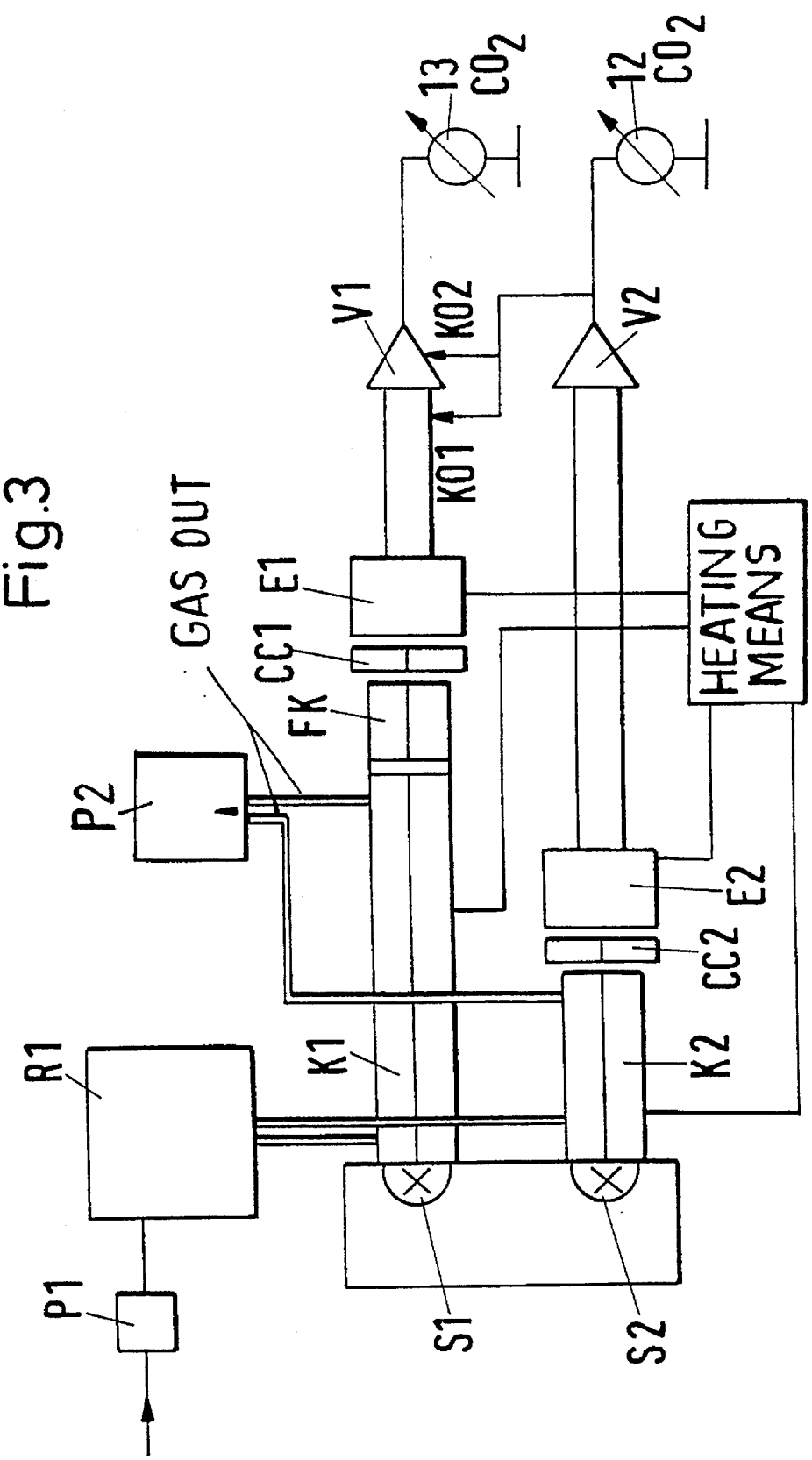
FIG. 3 is a schematic view of a measuring arrangement of NDIR spectrometer.

FIG. 3 of the drawing schematically shows the configuration according to the present invention of an NDIR spectrometer, wherein the subsequent electronic correction is illustrated symbolically. The configuration shows two ray paths, each having a ray source S1, S2. The upper ray path serves to measure the $^{13}CO_2$ portion and the lower ray path serves to measure the $^{12}CO_2$ portion.

Measuring vessels are arranged in the upper ray path as well as in the lower ray path. The gas to be analyzed is introduced in parallel to the measuring vessels. The gas to be analyzed is conducted through the vessel K1 as well as through the vessel K2 and is at the end also discharged together, i.e., in parallel. A filter vessel FK is arranged in the $^{13}CO_2$ ray path following the vessel K1. The filter vessel FK is filled in the measuring ray path with 100% by volume $^{12}CO_2$ and carries out the so-called positive optical filtering. A calibrating vessel CC1 which is arranged subsequently and can be swung into the ray path is filled with $^{13}CO_2$ in inert gas, such as $N_2$. The subsequently arranged detector E1 is filled with $^{13}CO_2$ in noble gas, such as argon, and, thus, is sensitized to $^{13}CO_2$. The electrical output of the detector is conducted through an amplifier V1 to a symbolically illustrated indicator or evaluator 13. A calibrating vessel CC2 is arranged in the second ray path following the vessel K2. The calibrating vessel CC2 is filled with $^{12}CO_2$ in inert gas, such as $N_2$, and can be swung into the ray path. The subsequently arranged detector E2 is filled with $^{12}CO_2$ in noble gas, such as argon. The calibrating vessels CC1, CC2 are hermetically sealed to contain the calibrating agents and gas mixtures therein.

In addition, a mixing reservoir R1 is provided at the gas entry. The gas to be measured is collected in the mixing reservoir R1 before entering the vessels K1 and K2. For example, a pressure pump P1 conveys the measuring gas to the reservoir R1. It would also be possible to arrange the pump P1 at the gas exit of the vessels K1 and K2 so that the gas to be measured is supplied directly to the reservoir R1 and is sucked by means of a suction pump P2 through the vessels K1 and K2. In general, it is important in this connection that the flow through the vessels takes place uniformly, although, as can be seen in FIG. 3, the volumes of the vessels K1 and K2 are different. The flow through the vessels must be uniform in the two vessels K1 and K2 because otherwise the electronic compensation according to the present invention between the $^{12}CO_2$ measuring duct and the $^{13}CO_2$ measuring duct would not produce useful results. In addition, for measuring gases which are saturated with water vapor, a particular development provides that the measuring vessels as well as the detectors are heated. This is useful because the measuring arrangement has a transverse sensitivity with respect to water vapor. This transverse sensitivity is prevented by the heating measure described above.

The electric output signal of the detector E2 is conducted to an amplifier V2. The output value KO1, KO2 of amplifier V2 is connected to the measuring signal evaluation of E1 in which, in addition to a rotation or a change of the amplification factor, an offset change is carried out. The specific manner in which the output value of the amplifier V2 is connected to the signal of the detector E1 is not significant to the invention and how such a connection can be made is readily within the knowledge of those skilled in the art. The electronic compensation can be carried out by an appropriate circuit. However, the electronic compensation can also be carried out supported by software in the manner described in connection with FIG. 1.

The invention is not limited by the embodiments described above which are presented as examples only but can be modified in various ways within the scope of protection defined by the appended patent claims.

What is claimed is:

1. A method of selectively determining an isotope portion of a measuring gas by means of non-dispersive infrared spectroscopy, the method comprising sensitizing the measuring gas in a first ray path to an isotope component $*A_xB_y$ and sensitizing the measuring gas in a second ray path to the isotope-pure measuring gas $A_xB_y$, electronically amplifying the measurement results, carrying out an additional optical filtering in the first ray path by a filter essentially filled with isotope-pure measuring gas $A_xB_y$, and using the electronic measuring value of the second ray path for influencing an amplification factor and an offset in the measurement result of the first ray path.

2. The method according to claim 1, wherein the elements of the measuring gas molecule are A=carbon, B=oxygen and the stoichiometric indexes are x=1 and y=2, and the isotope *A is the carbon isotope $^{13}C$.

3. The method according to claim 1, comprising conducting in a permanent flow the measuring gas including the isotope portion contained therein in the first and second ray paths over almost the entire longitudinal extension of measuring vessels provided in the ray paths, wherein a filter provided in the first ray path is essentially filled with the isotope-pure measuring gas and is hermetically sealed.

4. The method according to claim 3, wherein the step of conducting a permanent flow of the measuring gas includes conducting a measuring gas that is saturated with water vapor.

5. A non-dispersive infrared spectrometer comprising a first and a second ray path, each ray path comprising an infrared radiator, a measuring vessel and a detector, and amplification detectors for producing at an output thereof an electrical output signal the measuring vessel of the first ray path being longer than the measuring vessel of the second ray path, a filter vessel filled with gas primarily corresponding to the isotope-pure measuring gas being arranged between the measuring vessel and the detector of the first ray path for the selective determination of the isotope portion of a measuring gas, wherein the subsequent detector is sensitized to the isotope which is proportionately to be determined, and wherein the detector of the second ray path is sensitized to the isotope-pure measuring gas, the amplification detector of the second ray path having an output connected to the amplification detector of the first ray path so that a measured value of the second ray path can influence an amplification factor of the first ray path.

6. The non-dispersive infrared spectrometer according to claim 5, further comprising a calibration vessel arranged for calibration in front of the detector of the first ray path, the calibration vessel being filled with a gas mixture of the proportionately to be determined isotope of the measuring gas and an inert gas.

7. The non-dispersive infrared spectrometer according to claim 6, comprising another calibration vessel arranged for calibration in front of the detector of the second ray path, the another calibration vessel being filled with a gas mixture of the isotope-pure measuring gas and an inert gas.

8. The non-dispersive infrared spectrometer according to claim 7, wherein the inert gas is $N_2$.

9. The non-dispersive infrared spectrometer according to claim 7, wherein calibrating agents and gas mixtures of the calibrating vessels are contained hermetically sealed within the calibrating vessels.

10. The non-dispersive infrared spectrometer according to claim 9, wherein the infrared radiators, the measuring vessels and the detectors of the ray paths are arranged so that the ray paths are parallel and so that the measuring gas is introduced in an area at an end of an infrared radiator in parallel into a respective measuring ray path of the two measuring vessels and the measuring gas is discharged in parallel from the measuring vessels in an area of the detectors.

11. The non-dispersive infrared spectrometer according to claim 10, comprising a suction pump for maintaining flow of the measuring gas, the suction pump being provided at the gas outlet side of the measuring vessels.

12. The non-dispersive infrared spectrometer according to claim 9, comprising a pressure pump for maintaining flow through the measuring vessels.

13. The non-dispersive infrared spectrometer according to claim 12, comprising a mixing reservoir for the gas to be measured, the mixing reservoir being arranged in front of the measuring vessels.

14. The non-dispersive infrared spectrometer according to claim 5, wherein the detectors are opto-pneumatic detectors.

15. The non-dispersive infrared spectrometer according to claim 14, wherein the detector of the first ray path is filled with a mixture of noble gas and the isotope of the measuring gas to be determined.

16. The non-dispersive infrared spectrometer according to claim 15, wherein the detector of the second ray path is filled with a mixture of noble gas and the isotope-pure measuring gas.

17. The non-dispersive infrared spectrometer according to claim 16, wherein the noble gas is Argon.

* * * * *